United States Patent
Goldshtein et al.

(10) Patent No.: US 10,105,103 B2
(45) Date of Patent: Oct. 23, 2018

(54) REMOTELY POWERED SENSORY IMPLANT

(71) Applicant: VECTORIOUS MEDICAL TECHNOLOGIES LTD., Tel-Aviv (IL)

(72) Inventors: Oren Goldshtein, Nahariya (IL); Aharon Daffan, Jerusalem (IL); Ronny Winshtein, Ramat Hasharon (IL)

(73) Assignee: VECTORIOUS MEDICAL TECHNOLOGIES LTD., Tel-Aviv (IL)

( * ) Notice: Subject to any disclaimer, the term of this patent is extended or adjusted under 35 U.S.C. 154(b) by 337 days.

(21) Appl. No.: 14/766,750

(22) PCT Filed: Mar. 24, 2014

(86) PCT No.: PCT/IB2014/060085
§ 371 (c)(1),
(2) Date: Aug. 9, 2015

(87) PCT Pub. No.: WO2014/170771
PCT Pub. Date: Oct. 23, 2014

(65) Prior Publication Data
US 2016/0022216 A1 Jan. 28, 2016

Related U.S. Application Data

(60) Provisional application No. 61/838,357, filed on Jun. 24, 2013, provisional application No. 61/813,575, filed on Apr. 18, 2013.

(51) Int. Cl.
*H04B 5/00* (2006.01)
*A61B 5/00* (2006.01)
(Continued)

(52) U.S. Cl.
CPC .......... *A61B 5/6869* (2013.01); *A61B 5/0215* (2013.01); *A61B 5/6884* (2013.01);
(Continued)

(58) Field of Classification Search
CPC .................. H02J 7/025; H04B 5/00
(Continued)

(56) References Cited

U.S. PATENT DOCUMENTS 3,264,861 A 8/1966 Miles
4,127,110 A 11/1978 Bullara
(Continued)

FOREIGN PATENT DOCUMENTS

JP S5973747 A 4/1984
KR 20040060577 A 7/2004
(Continued)

OTHER PUBLICATIONS

International Application # PCT/IB2013/060038 Search Report dated May 1, 2014.
(Continued)

*Primary Examiner* — Ayodeji Ayotunde
(74) *Attorney, Agent, or Firm* — D. Kligler IP Services Ltd.

(57) ABSTRACT

An implant (110) includes an antenna unit (130) and an encapsulation. The antenna unit includes an elongated ferrite core (142) having a first length and an antenna coil (146) wound around the ferrite core, and is configured to communicate with an external unit (120) using inductive coupling of a magnetic field. The encapsulation encapsulates the antenna unit, and includes one or more openings (134) that are aligned with the ferrite core and have respective second lengths that are equal to or greater than the first length of the ferrite core.

13 Claims, 5 Drawing Sheets

(51) Int. Cl.
  *H02J 50/90* (2016.01)
  *H02J 50/80* (2016.01)
  *H02J 50/70* (2016.01)
  *H02J 50/12* (2016.01)
  *A61B 5/0215* (2006.01)
  *H02J 7/06* (2006.01)
  *H02J 5/00* (2016.01)

(52) U.S. Cl.
  CPC .............. *A61B 5/7217* (2013.01); *H02J 7/06* (2013.01); *H02J 50/12* (2016.02); *H02J 50/70* (2016.02); *H02J 50/80* (2016.02); *H02J 50/90* (2016.02); *A61B 2560/0219* (2013.01); *A61B 2562/02* (2013.01); *H02J 5/005* (2013.01)

(58) Field of Classification Search
  USPC ........................................................ 455/41.1
  See application file for complete search history.

(56) References Cited

U.S. PATENT DOCUMENTS

| | | | |
|---|---|---|---|
| 4,206,761 A | 6/1980 | Cosman | |
| 4,237,900 A | 12/1980 | Schulman et al. | |
| 4,256,094 A | 3/1981 | Kapp et al. | |
| 4,377,851 A | 3/1983 | McNamara | |
| 4,432,372 A | 2/1984 | Monroe | |
| 4,519,401 A | 5/1985 | Ko et al. | |
| 4,743,836 A | 5/1988 | Grzybowski et al. | |
| 4,791,934 A | 12/1988 | Brunnett | |
| 4,881,939 A | 11/1989 | Newman | |
| 5,105,190 A | 4/1992 | Kip et al. | |
| 5,113,868 A | 5/1992 | Wise et al. | |
| 5,480,412 A | 1/1996 | Mouchawar et al. | |
| 5,493,470 A | 2/1996 | Zavracky et al. | |
| 5,514,171 A | 5/1996 | Hoegnelid et al. | |
| 5,564,434 A | 10/1996 | Halperin et al. | |
| 5,942,692 A | 4/1999 | Haase et al. | |
| 6,015,386 A | 1/2000 | Kensey et al. | |
| 6,025,725 A | 2/2000 | Gershenfeld et al. | |
| 6,051,853 A | 4/2000 | Shimada et al. | |
| 6,111,520 A | 8/2000 | Allen et al. | |
| 6,113,553 A | 9/2000 | Chubbuck | |
| 6,171,252 B1 | 1/2001 | Roberts | |
| 6,275,681 B1 | 8/2001 | Vega et al. | |
| 6,309,350 B1 | 10/2001 | Vantassel et al. | |
| 6,389,371 B1 | 5/2002 | Tsuchiya et al. | |
| 6,409,674 B1 | 6/2002 | Brockway et al. | |
| 6,622,041 B2 | 9/2003 | Terry, Jr. et al. | |
| 6,667,725 B1 | 12/2003 | Simons et al. | |
| 6,772,070 B2 | 8/2004 | Gilmanshin et al. | |
| 6,778,070 B1 | 8/2004 | Thomas | |
| 6,926,670 B2 | 8/2005 | Rich et al. | |
| 6,936,053 B1 | 8/2005 | Weiss | |
| 7,086,270 B2 | 8/2006 | Weinberg et al. | |
| 7,149,587 B2 | 12/2006 | Wardle et al. | |
| 7,216,048 B2 | 5/2007 | Wang et al. | |
| 7,256,695 B2 | 8/2007 | Hamel et al. | |
| 7,317,951 B2 | 1/2008 | Schneider et al. | |
| 7,335,161 B2 | 2/2008 | Von Arx et al. | |
| 7,413,547 B1 | 8/2008 | Lichtscheidl et al. | |
| 7,425,749 B2 | 9/2008 | Hartzell et al. | |
| 7,509,169 B2 | 3/2009 | Eigler et al. | |
| 7,515,971 B1 | 4/2009 | Doan | |
| 7,628,054 B2 | 12/2009 | Hajishah et al. | |
| 7,634,319 B2 | 12/2009 | Schneider et al. | |
| 7,635,338 B2 | 12/2009 | Eide | |
| 7,647,831 B2 | 1/2010 | Corcoran et al. | |
| 7,677,107 B2 | 3/2010 | Nunez et al. | |
| 7,678,123 B2 | 3/2010 | Chanduszko | |
| 7,684,872 B2 | 3/2010 | Carney et al. | |
| 7,686,768 B2 | 3/2010 | Bodecker et al. | |
| 7,762,138 B2 | 7/2010 | Zdeblick et al. | |
| 7,860,579 B2 | 12/2010 | Goetzinger et al. | |
| 7,899,550 B1 | 3/2011 | Doan et al. | |
| 8,021,307 B2 | 9/2011 | White et al. | |
| 8,118,749 B2 | 2/2012 | White et al. | |
| 8,154,389 B2 | 4/2012 | Rowland et al. | |
| 8,285,204 B2 | 10/2012 | Martin | |
| 8,353,841 B2 | 1/2013 | White et al. | |
| 8,355,777 B2 | 1/2013 | White et al. | |
| 8,432,265 B2 | 4/2013 | Rowland et al. | |
| 8,493,187 B2 | 7/2013 | Rowland et al. | |
| 8,810,405 B2 | 8/2014 | Stevenson et al. | |
| 8,894,582 B2 | 11/2014 | Nunez et al. | |
| 9,513,609 B2 | 12/2016 | Thueringer et al. | |
| 9,662,066 B2 | 5/2017 | Ledet et al. | |
| 9,730,764 B2 | 8/2017 | Van Der Weide et al. | |
| 2001/0018596 A1 | 8/2001 | Selmon et al. | |
| 2002/0045921 A1 | 4/2002 | Wolinsky et al. | |
| 2002/0077556 A1 | 6/2002 | Schwartz | |
| 2002/0120200 A1 | 8/2002 | Brockway et al. | |
| 2003/0097073 A1 | 5/2003 | Bullister et al. | |
| 2003/0139677 A1 | 7/2003 | Fonseca et al. | |
| 2004/0103906 A1 | 6/2004 | Schulman et al. | |
| 2005/0004644 A1 | 1/2005 | Kelsch et al. | |
| 2005/0065589 A1 | 3/2005 | Schneider et al. | |
| 2005/0088184 A1 | 4/2005 | Burdick et al. | |
| 2005/0288596 A1 | 12/2005 | Eigler et al. | |
| 2006/0116572 A1 | 6/2006 | Case | |
| 2006/0206178 A1 | 9/2006 | Kim | |
| 2006/0229488 A1 | 10/2006 | Ayre et al. | |
| 2006/0287602 A1 | 12/2006 | O'Brien et al. | |
| 2007/0049980 A1 | 3/2007 | Zielinski et al. | |
| 2007/0049984 A1 | 3/2007 | Osypka | |
| 2007/0118038 A1 | 5/2007 | Bodecker et al. | |
| 2007/0135826 A1 | 6/2007 | Zaver et al. | |
| 2007/0142727 A1 | 6/2007 | Zhang et al. | |
| 2007/0179583 A1 | 8/2007 | Goetzinger et al. | |
| 2007/0255144 A1 | 11/2007 | Tulkki et al. | |
| 2007/0261496 A1 | 11/2007 | Jonsson et al. | |
| 2007/0293779 A1 | 12/2007 | Bardy | |
| 2008/0004673 A1 | 1/2008 | Rossing et al. | |
| 2008/0033527 A1 | 2/2008 | Nunez et al. | |
| 2008/0045242 A1 | 2/2008 | Dekock et al. | |
| 2008/0064966 A1 | 3/2008 | Brockway et al. | |
| 2008/0092663 A1 | 4/2008 | Corcoran et al. | |
| 2008/0139959 A1 | 6/2008 | Miethke et al. | |
| 2008/0154101 A1 | 6/2008 | Jain et al. | |
| 2008/0269573 A1 | 10/2008 | Najafi et al. | |
| 2008/0281212 A1 | 11/2008 | Nunez et al. | |
| 2009/0005859 A1 | 1/2009 | Keilman | |
| 2009/0013791 A1 | 1/2009 | Zdeblick et al. | |
| 2009/0024042 A1 | 1/2009 | Nunez et al. | |
| 2009/0030291 A1 | 1/2009 | O'Brien et al. | |
| 2009/0036754 A1 | 2/2009 | Pons et al. | |
| 2009/0069648 A1 | 3/2009 | Irazogui et al. | |
| 2009/0093729 A1 | 4/2009 | Zhang et al. | |
| 2009/0192381 A1 | 7/2009 | Brockway et al. | |
| 2009/0275924 A1 | 11/2009 | Lattanzio et al. | |
| 2009/0281520 A1 | 11/2009 | Highley et al. | |
| 2009/0299216 A1 | 12/2009 | Chen et al. | |
| 2010/0179449 A1 | 7/2010 | Chow et al. | |
| 2010/0179618 A1 | 7/2010 | Marnfeldt et al. | |
| 2010/0249756 A1 | 9/2010 | Koh | |
| 2010/0280330 A1 | 11/2010 | Samuelsson et al. | |
| 2011/0021887 A1 | 1/2011 | Crivelli et al. | |
| 2011/0040206 A1 | 2/2011 | Burger et al. | |
| 2011/0043336 A1 | 2/2011 | Gueorguiev | |
| 2011/0133894 A1* | 6/2011 | Hennig .................. | H02J 50/20 340/10.1 |
| 2011/0160560 A1 | 6/2011 | Stone | |
| 2011/0264217 A1 | 10/2011 | Oureshi | |
| 2011/0303229 A1 | 12/2011 | Najafi et al. | |
| 2012/0022507 A1 | 1/2012 | Najafi et al. | |
| 2012/0319862 A1 | 12/2012 | Nagy et al. | |
| 2013/0107913 A1 | 5/2013 | Savoj | |
| 2013/0215979 A1 | 8/2013 | Yakovlev et al. | |
| 2013/0222153 A1 | 8/2013 | Rowland et al. | |
| 2013/0233086 A1 | 9/2013 | Besling et al. | |
| 2014/0028467 A1 | 1/2014 | Nagy et al. | |
| 2014/0062717 A1 | 3/2014 | Mudumbai et al. | |
| 2014/0155710 A1 | 6/2014 | Rowland et al. | |
| 2014/0306807 A1 | 10/2014 | Rowland et al. | |

(56) References Cited

U.S. PATENT DOCUMENTS

| | | | |
|---|---|---|---|
| 2015/0290465 A1* | 10/2015 | Mashiach | A61N 1/0558 607/61 |
| 2016/0058324 A1 | 3/2016 | Cao et al. | |
| 2017/0018172 A1 | 1/2017 | He et al. | |
| 2017/0118543 A1 | 4/2017 | Ha et al. | |
| 2017/0155429 A1 | 6/2017 | Hung et al. | |

FOREIGN PATENT DOCUMENTS

| | | | |
|---|---|---|---|
| WO | 2006042280 A2 | 4/2006 | |
| WO | 2008042229 A2 | 4/2008 | |
| WO | 2008127525 A1 | 10/2008 | |
| WO | 2009097485 A1 | 8/2009 | |
| WO | 2011053246 A1 | 5/2011 | |
| WO | 2012078861 A2 | 6/2012 | |
| WO | 2012090206 A2 | 7/2012 | |
| WO | 2014006471 A2 | 1/2014 | |
| WO | 2014145012 A2 | 9/2014 | |
| WO | 2014170771 A1 | 10/2014 | |

OTHER PUBLICATIONS

Dai et al., "Capacitive Micro Pressure Sensor Integrated with a Ring Oscillator Circuit on Chip", Sensors 2009, vol. 9, chapter 12, pp. 10158-10170, Jan. 1, 2009.

Yameogo et al., "Self Calibrating pressure sensor for biomedical applications", IEEE Sensors Conference, pp. 691-694, Oct. 25-28, 2009.

Goldshtein et al., U.S. Appl. No. 14/437,198, filed Apr. 21, 2015.

International Application # PCT/IB2014/060085 Search Report dated Jul. 8, 2014.

Olivo et al., "Electronic implants: Power delivery and management", Integrated Systems Laboratory—EPFL, 6 pages, Mar. 22, 2013.

Mandal et al., "Power-Efficient Impedance-Modulation Wireless Data Links for Biomedical Implants", IEEE Transactions on Biomedical Circuits and Systems, vol. 2, No. 4, pp. 301-315, Dec. 4, 2008.

Bradford et al., "Wireless Power and Data Transmission for a Pressure Sensing Medical Implant", Proceedings BMT 2010, Rostock, Germany, 4 pages, Oct. 6-8, 2010.

International Application # PCT/IB2015/060054 Search Report dated Mar. 21, 2016.

European Application # 13855953.9 Search Report dated May 30, 2016.

Cleven et al., "A Novel Fully Implantable Wireless Sensor System for Monitoring Hypertension Patients", IEEE Transactions on Biomedical Engineering vol. 59, No. 11, pp. 3124-3130, Nov. 2012.

Jiang., "Design challenges of implantable pressure monitoring system", Frontiers of Neuroscience, vol. 4, Art 29, pp. 1-4, Feb. 26, 2010.

Simons et al., "Spiral chip implantable radiator and printed loop external receptor for RF telemetry in bio-sensor systems", In Radian and Wireless Conference IEEE, 12 pages, 2004.

Simons et al., "Wearable wireless telemetry system for implantable bio-MEMS sensors", In Engineering in Medicine and Biology Society Conference, IEEE, 12 pages, 2006.

Maxim, "Approaches for Compensating Span and Offset in Pressure Sensors", Application Note 743, 5 pages, Mar. 27, 2001.

Coosemans., "An autonomous bladder pressure monitoring system", Katholike Universiteit Leuven, Department ESAT-MICAS, Kasteelpark Arenberg, Belgium, Sensors and Actuators A: Physical, Elsevier BV, vol. 123-124, pp. 155-161, Sep. 23, 2005.

European Application # 14785775.9 Search Report dated Oct. 24, 2016.

JP Application # 2015-541286 Office Action dated Mar. 8, 2017.

Ziaie et al., "An Implantable Microsystem for Tonometric Blood Pressure Measurement", Biomedical Microdevices, vol. 3, Issue 4, pp. 285-292, Dec. 2001.

European Application # 13855953.9 office action dated Aug. 18, 2017.

* cited by examiner

REMOTELY POWERED SENSORY IMPLANT

CROSS-REFERENCE TO RELATED APPLICATIONS

This application claims the benefit of U.S. Provisional Patent Application 61/813,575, filed Apr. 18, 2013, and U.S. Provisional Patent Application 61/838,357, filed Jun. 24, 2013, whose disclosures are incorporated herein by reference.

FIELD OF THE INVENTION

The present invention relates generally to medical devices, and particularly to sensory implants.

BACKGROUND OF THE INVENTION

Various systems use inductive coupling techniques for providing electrical power and communicating with miniature devices, such as medical implants and identification tags. For example, U.S. Pat. No. 5,105,190, whose disclosure is incorporated herein by reference, describes an electromagnetic identification system in which a transmitter generates an electromagnetic interrogation field in a detection zone. At least one responder is provided capable of disturbing the interrogation field. A detection circuit detects a disturbance of the interrogation field caused by a responder. The responder is a single receiver circuit which responds to the interrogation field which supplies energy to activate a digital encoding circuit having a binary-code defining circuit. The encoding circuit is arranged, in operation, through a switch to vary the electrical characteristics of the receiver circuit to generate a code signal that is detectable by the detection circuit. The encoding circuit is arranged to control the switch during the pre-determined periods of time for varying the electrical characteristics of the receiver circuit. A programmer is provided to modulate the transmitter to generate a modulated interrogation field.

U.S. Pat. No. 6,778,070, whose disclosure is incorporated herein by reference, describes a remote transmission apparatus for a portable object equipped with an antenna and connected by inductive coupling to a fixed station. A data processor processes and stores data concerning the portable object, a voltage rectifier transforms the AC voltage supplied by the antenna of the portable object into a DC voltage carried by a power line to the data processor, a voltage regulator regulates the DC voltage provided by the rectifier, and a modulator modulates the signals to be transmitted. The modulator comprises a transistor connected to an electronic dipole that causes a drop in voltage between the input and output of the modulator, the modulator being connected to the input of the voltage regulator to control the voltage on the terminals of the antenna in order to modulate the current flowing in the antenna.

U.S. Pat. No. 8,285,204, whose disclosure is incorporated herein by reference, describes a contactless data transmission device that includes an antenna circuit supplying an alternating voltage in the presence of an alternating excitation field, a charge modulation transistor having a control terminal receiving a charge modulation signal having at least one low state and one high state, and a conduction terminal receiving the alternating voltage. The device includes a circuit for supplying a boosted direct voltage greater than a peak value of the alternating voltage supplied by the antenna circuit, and a circuit for applying to the control terminal of the charge modulation transistor a charge modulation signal which, in the high state, has a voltage level equal to the boosted direct voltage.

SUMMARY OF THE INVENTION

An embodiment of the present invention provides an implant including an antenna, circuitry, and a voltage clamping element. The antenna is configured to communicate with an external unit using inductive coupling of a magnetic field. The circuitry is configured to produce data for transmission to the external unit, to modulate a load impedance applied to the antenna as a function of the data so as to transmit the data, and to receive electrical power from the magnetic field via the antenna for powering the circuitry. The voltage clamping element is coupled to clamp a voltage induced by the magnetic field across the antenna so as to maximize a modulation depth of the load impedance, and so as to regulate the electrical power that powers the circuitry.

In some embodiments, the circuitry includes a modulation switch that is connected in series with the voltage clamping element across the antenna, such that the voltage clamping element applies a low load impedance across the antenna only when the modulation switch is closed. In an embodiment, the voltage clamping element includes at least one Zener diode. In another embodiment, the voltage clamping element includes one or more diodes connected in forward conduction relative to the voltage. In yet another embodiment, the voltage clamping element includes a transistor circuit.

There is also provided, in accordance with an embodiment of the present invention, an implant including an antenna and circuitry. The antenna is configured to communicate with an external unit using inductive coupling of a magnetic field. The circuitry is configured to receive electrical energy from the magnetic field via the antenna for powering the circuitry, to produce data for transmission to the external unit, and to modulate a load impedance applied to the antenna as a function of the data so as to transmit the data, while balancing the data to be modulated such that the electrical energy received from the magnetic field meets a power requirement of the circuitry regardless of the data.

In some embodiments, the circuitry is configured to balance the data by modulating the load, for each data value, with a respective waveform comprising a positive-voltage part and a negative-voltage part. In some embodiments, the circuitry is configured to balance the data by modulating each data value twice with opposite polarities.

There is further provided, in accordance with an embodiment of the present invention, an implant including a pressure sensor, a noise compensation antenna and circuitry. The pressure sensor is configured to measure an ambient pressure in a vicinity of the implant. The noise compensation antenna is configured to receive first interference that is indicative of second interference received by the pressure sensor. The circuitry is configured to translate the measured ambient pressure into a signal while compensating for the second interference using the first interference, and to transmit the signal to an external unit.

In some embodiments, the pressure sensor is configured to vary a capacitance thereof depending on the ambient pressure, and the circuitry is configured to vary a frequency of the signal as a function of the capacitance while canceling the second interference using the first interference. In an embodiment, the circuitry includes a component that is programmable by the external unit for calibrating cancellation of the second interference using the first interference.

There is also provided, in accordance with an embodiment of the present invention, an implant includes an antenna unit and an encapsulation. The antenna unit includes an elongated ferrite core having a first length and an antenna coil wound around the ferrite core, and is configured to communicate with an external unit using inductive coupling of a magnetic field. The encapsulation encapsulates the antenna unit, and includes one or more openings that are aligned with the ferrite core and have respective second lengths that are equal to or greater than the first length of the ferrite core.

In some embodiments, the implant further includes a data processing unit that is configured to produce data for transmission to the external unit, and the antenna unit is configured to transfer the data to the external unit using the inductive coupling. In some embodiments, the implant further includes a data processing unit, and the antenna unit is configured to receive, using the inductive coupling, electrical energy for powering the data processing unit.

In a disclosed embodiment, the second lengths are greater than the first length by at least twice a diameter of the ferrite core. In an example embodiment, the one or more openings include multiple openings that are distributed around the encapsulation surrounding the antenna unit. In another embodiment, the one or more openings include two or more openings that are positioned at two or more respective longitudinal positions along the encapsulation.

In an example embodiment, the antenna unit includes two or more ferrite cores having two or more respective antenna coils wound thereon, such that the two or more ferrite cores are aligned with the two or more respective openings in the encapsulation. In some embodiments, the openings are sealed with a non-metallic material. In some embodiments the encapsulation is metallic.

There is additionally provided, in accordance with an embodiment of the present invention, a method for producing an implant. The method includes providing an antenna unit, which includes an elongated ferrite core having a first length and an antenna coil wound around the ferrite core. The antenna unit is encapsulated with an encapsulation, which includes one or more openings that are aligned with the ferrite core and have respective second lengths that are equal to or greater than the first length of the ferrite core.

There is additionally provided, in accordance with an embodiment of the present invention, a method for operating an implant. The method includes producing data for transmission to an external unit, and modulating a load impedance applied to an antenna as a function of the data so as to transmit the data to the external unit using inductive coupling of a magnetic field. Electrical power for powering the implant is received via the antenna from the magnetic field. A voltage induced by the magnetic field across the antenna is clamped using a voltage clamping element, so as to maximize a modulation depth of the load impedance, and so as to regulate the electrical power.

There is also provided, in accordance with an embodiment of the present invention, a method for operating an implant. The method includes receiving via an antenna electrical energy for powering the implant from a magnetic field of an external unit. Data for transmission to the external unit is produced, and a load impedance applied to the antenna is modulated as a function of the data so as to transmit the data, while balancing the data to be modulated such that the electrical energy received from the magnetic field meets a power requirement of the circuitry regardless of the data.

There is further provided, in accordance with an embodiment of the present invention, a method for operating an implant. The method includes measuring an ambient pressure in a vicinity of the implant using a pressure sensor. First interference, which is indicative of second interference received by the pressure sensor, is received using a noise compensation antenna. The measured ambient pressure is translated into a signal while compensating for the second interference using the first interference. The signal is transmitted to an external unit.

The present invention will be more fully understood from the following detailed description of the embodiments thereof, taken together with the drawings in which:

DETAILED DESCRIPTION OF EMBODIMENTS

Overview

Embodiments of the present invention that are described herein provide improved sensory implants and associated methods. The disclosed embodiments refer mainly to cardiac implants that measure the ambient blood pressure in a heart of a patient, but the disclosed techniques can be used in various other types of implants and applications.

The disclosed implants typically use magnetic-field inductive coupling for communicating with an external unit, and for receiving electrical energy from the external unit. The implant typically comprises an antenna unit in which the magnetic field of the external unit is induced. In some embodiments, the antenna unit comprises an antenna coil wound around a ferrite core, and an encapsulation that encapsulates the antenna unit. The encapsulation is typically metallic, and comprises one or more openings that are aligned with the ferrite core and have lengths that are equal to or greater than the length of the ferrite core. These dimension relations cause minimal distortion to the magnetic field, and therefore achieve highly efficient inductive coupling. As a result, antenna size can be reduced both on the implant side and on the external unit side, and lower-energy magnetic fields can be used.

In some embodiments, the implant comprises circuitry that transmits data (e.g., measured pressure readings) to the external unit by modulating the load impedance of the implant antenna. In particular, the circuitry comprises a voltage clamping element that clamps the voltage induced by the magnetic field across the implant antenna. The voltage clamping element plays a dual role—Maximizing the modulation depth of the load modulation, and regulating the received electrical power. As a result, implant size and cost can be reduced, without compromising communication reliability or voltage regulation performance.

In some embodiments, the implant modulates the load of the antenna using a balanced modulation scheme, which ensures that sufficient electrical energy can be extracted from the magnetic field at any time, regardless of the data. This sort of modulation avoids scenarios in which a problematic data pattern reduces the induced voltage for a long period of time. In other disclosed embodiments the implant comprises a noise compensation pad, which is used by the implant circuitry to cancel Radio Frequency (RF) interference pick-up by the pressure sensor.

System Description

Figure 1:
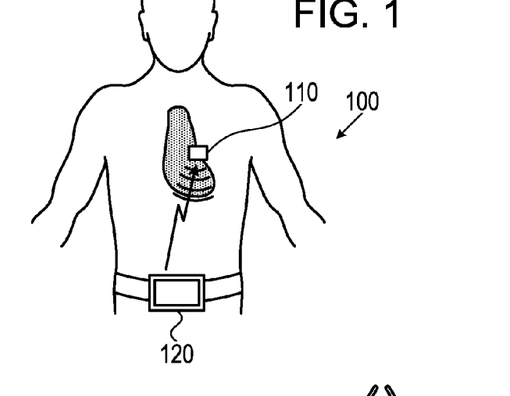
FIG. 1 is a block diagram that schematically illustrates a medical monitoring system that includes a sensory implant, in accordance with an embodiment of the present invention.

FIG. 1 is a block diagram that schematically illustrates a medical monitoring system 100 that includes a sensory implant 110, in accordance with an embodiment of the present invention. In the present example, implant 100 is implanted at a desired location in the heart of a patient, and is used for measuring the ambient blood pressure in its vicinity.

In an example embodiment, implant 110 is implanted in a wall of the left atrium (LA). Alternatively, the implant may be positioned at any other suitable location in the heart. Further alternatively, the disclosed techniques can be used for measuring pressure in various other organs, and for measuring various other suitable physiological parameters of the patient.

System 100 further comprises an external unit 120, which is configured to communicate with implant 100 and to provide electrical power to the implant circuitry. In the present example, unit 120 is fitted on a belt that is worn by the patient. The belt also comprises the antenna of the external unit. FIG. 1 shows the belt worn on the patient's waist, for the sake of clarity. In practice, the belt should typically be worn such that the implant is (at least approximately) surrounded by the belt, i.e., located in the plane defined by the belt. In an example embodiment, the belt may be worn diagonally over the neck and one shoulder of the patient. Alternatively, however, any other suitable configuration can be used.

Implant 110 typically does not comprise an internal power source. The internal circuitry of the implant is powered by energy that is provided by external unit 120 using inductive coupling. Typically, the external unit generates an Alternating Current (AC) magnetic field using its antenna. This magnetic field induces an AC voltage across an antenna of the implant, and this voltage is then rectified and used for powering the implant circuitry. At the same time, the implant sends data (e.g., measurement results of ambient blood pressure) by modulating the load impedance of its antenna, modulation that is sensed by the external unit. These mechanisms are explained in detail below.

Figure 2:
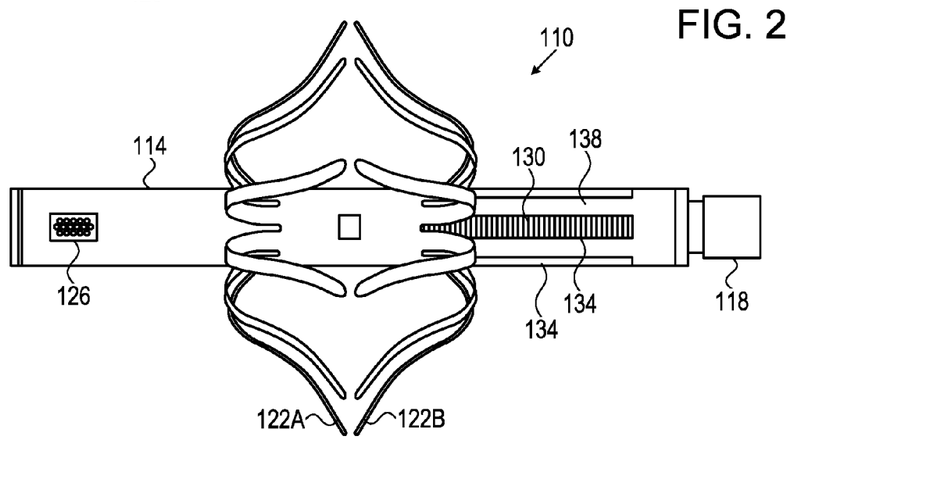
FIG. 2 is a schematic side view of a sensory implant, in accordance with an embodiment of the present invention.

FIG. 2 is a schematic side view of implant 110, in accordance with an embodiment of the present invention. Implant 100 comprises an elongate body 114. The implant is designed to be inserted half-way through a wall of a cardiac chamber, and then mounted and retained in the wall.

For this purpose, the implant comprises two sets of "spider-leg" arms denoted 122A and 122B. During delivery of the implant, legs 122A and 122B are collapsed and held closely around body 114. After delivery, the arms extend to the expanded position shown in the figure, such that the heart wall is locked between arms 122A and arms 122B. The left-hand-side of the implant (the side of arms 122A) is located in the interior of the heart, and the right-hand-side of the implant (the side of arms 122B) is located outside the heart.

Additional aspects relating to delivery and retention of implants of this sort are addressed in PCT Application PCT/IL2011/050082, entitled "Method and systems for delivering and deploying a sensory implant in tissues," and PCT Application PCT/IB2013/001401, entitled "Organ wall retention mechanism for implants," whose disclosures are incorporated herein by reference.

In the example of FIG. 2, implant 110 comprises an interconnection member 118 for detachably connecting to a suitable delivery means, e.g., a needle or catheter. Body 114 of the implant typically comprises a metallic encapsulation. The internal circuitry of the implant is encapsulated in body 114. Two elements of the circuitry, namely a pressure sensor 126 and an antenna unit 130, are seen in the figure.

In some embodiments, one or more openings 134 are formed in the metallic encapsulation of body 114, in the vicinity of antenna unit 130, between wall sections 138 of the encapsulation. Openings 134 are designed to minimize distortion and attenuation of the magnetic field that is used for communication and power delivery between antenna unit 130 and external unit 120. Design considerations for openings 134 are given further below.

Dimensioning of Antenna Ferrite Core and Openings

Figure 3:
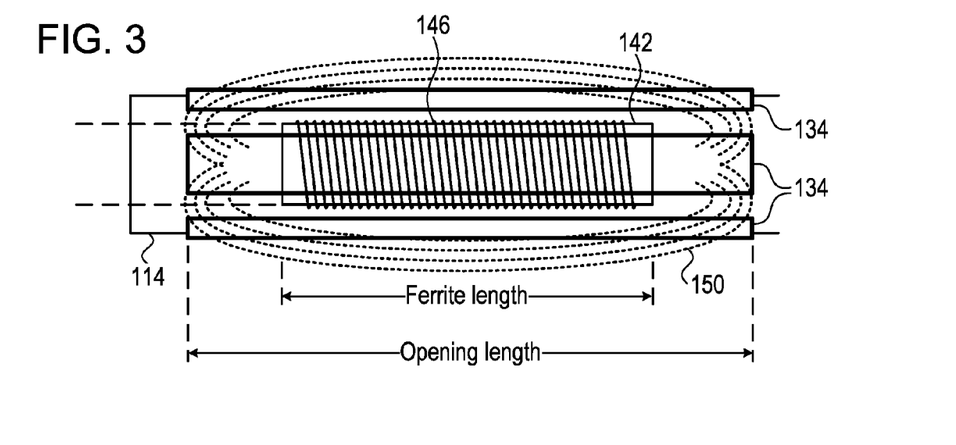
FIG. 3 is a schematic illustration of an antenna unit in a sensory implant, in accordance with an embodiment of the present invention.

FIG. 3 is a schematic illustration of antenna unit 130 in sensory implant 110, in accordance with an embodiment of the present invention. In the present example, antenna unit 130 comprises an antenna coil 146 that is wound around a ferrite core 142. Core 142 and coil 146 are aligned with openings 134 of body 114. The figure shows typical magnetic field lines 150 resulting from this configuration.

The inventors have found that certain relations between the length of openings 134 and the length of ferrite core 142 result in high performance, i.e., minimal distortion and attenuation of the magnetic field. Moreover, it has been found that the field distortion depends mainly on the geometrical relation between openings 134 and ferrite core 142, and is less sensitive to the geometry of coil 146.

In order to meet the above conditions, in some embodiments the length of openings 134 is set to be equal to or greater than the length of ferrite core 142. In an example embodiment, the length of openings 134 is greater than the length of ferrite core 142 by at least twice the diameter of the ferrite core. These length relations, however, are provided only by way of example. In alternative embodiments, other suitable geometries of the openings and the ferrite core can be used.

In one non-limiting example, body 114 has a diameter of 3 mm, ferrite core 142 has a diameter of 0.7 mm and a length of 7 mm, and openings 134 each have a length of 9 mm and a width of 0.5 mm. Alternatively, however, any other suitable dimensions can be used.

The example of FIG. 3 shows a single ferrite core, a single coil and a specific arrangement of openings, for the sake of conceptual clarity. In alternative embodiments, any other suitable configuration can be used. For example, body 114 may comprise any suitable number of openings 134. In some embodiments, as seen in FIG. 3, the openings are distributed around body 114, i.e., around the encapsulation that surrounds the antenna unit. In other embodiments, two or more openings 134 may be distributed longitudinally along the encapsulation. In some embodiments, openings 134 may be distributed both along and around body 114.

Further alternatively, in some embodiments antenna unit 130 comprises two or more ferrite cores 142, and two or more respective antenna coils 146 wound on the cores. In these embodiments, the ferrite cores are aligned with respective openings 134. Typically, openings 134 are sealed with a suitable non-metallic material, e.g., silicone such as silicone rubber, adhesive such as epoxy, nylon, polyurethane, polyester, PEEK, polyethylene, UHMWPE, polypropylene, PTFE, PMMA, EVA, PDMS, PU, PET, PEO, PEG or polysulphone.

The antenna unit and encapsulation configurations above are depicted purely by way of example. In alternative embodiments, implant 110 may comprise any other suitable antenna unit and/or encapsulation.

Control Circuitry—Voltage Regulation, Load Modulation & Capacitance-to-Frequency Conversion As noted above, the magnetic-field inductive coupling between external unit 120 and implant 110 is used for two purposes: Supplying the implant with electrical power for operating its internal circuitry, and transmitting data (e.g., measurement results) from the implant to the external unit.

Implant 110 thus comprises circuitry that performs both functions. Supply of electrical power is performed by rectifying and regulating the AC voltage that is induced in the implant's antenna by the AC magnetic field. Transmission of data is performed using "load modulation"—by modulating the load impedance seen by the implant's antenna. Modulating the antenna load impedance modulates the amount of energy drawn by the implant from the magnetic field. These changes in energy consumption are sensed by the external unit and demodulated, so as to decode the data sent by the implant.

Figure 4:
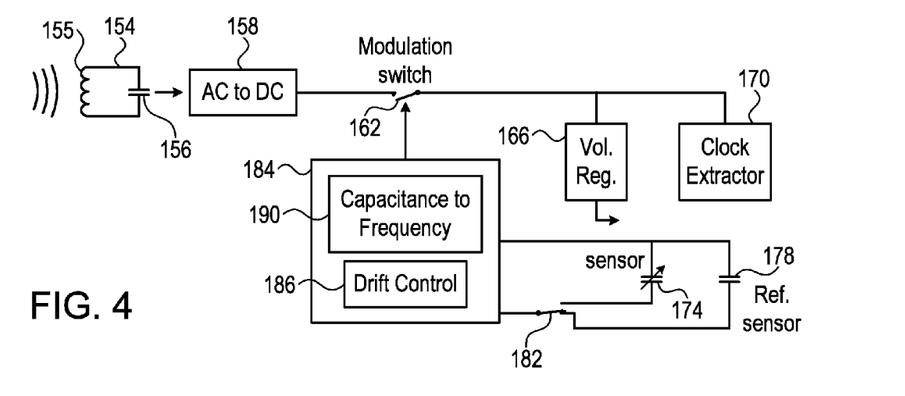
FIG. 4 is a block diagram that schematically illustrates control circuitry of a sensory implant, in accordance with an embodiment of the present invention.

FIG. 4 is a block diagram that schematically illustrates some of the internal circuitry of implant 110, in accordance with an embodiment of the present invention. In this embodiment, the implant comprises an antenna coil 155 that senses the magnetic field generated by the external unit.

In an example embodiment, coil 155 is connected to a capacitor 156, jointly forming a resonant circuit 154. The inductance of coil 155 and the capacitance of capacitor 156 are chosen such that the resonance frequency of circuit 154 matches the frequency of the AC magnetic field. In alternative embodiments, however, capacitor 156 can be omitted.

A rectifier 158 rectifies the AC voltage induced in circuit 154, so as to produce a Direct Current (DC) waveform. A voltage regulator 166 regulates the DC waveform, so as to produce a stable and regulated DC voltage. This voltage is used for powering the various implant components. In some embodiments, a clock extraction module 170 extracts a clock signal from the voltage induced in the antenna coil. The extracted clock signal is used for clocking the various digital components of the implant circuitry.

Implant 110 further comprises a pressure sensor 174, which is exposed to the blood and senses the ambient blood pressure. In the present example, sensor 174 comprises a Micro-Electromechanical System (MEMS) capacitance-based pressure sensor whose capacitance varies as a function of the ambient pressure. In this embodiment, sensor 174 comprises a capacitor in which one of the electrodes comprises a deformable membrane that deforms as a function of the ambient pressure. The deformation changes the sensor capacitance. In alternative embodiments, other suitable sensor types can also be used.

In some embodiments, the implant further comprises a reference pressure sensor 178 for calibration purposes. Reference sensor 178 may comprise, for example, a MEMS sensor that similar to sensor 174 but is not exposed to the ambient pressure. Comparison of the capacitances of the two sensors enables calibration of the pressure measurements of sensor 174 over operating conditions such as voltage and temperature. In these embodiments, the implant circuitry may perform alternate pressure measurements using sensors 174 and 178, using a selection switch 182.

In some embodiments, the implant comprises a processing circuit 184, which comprises a drift control unit 186 and a Capacitance-to-Frequency (C-to-F) conversion unit. Drift control unit 186 compensates for changes in the pressure-capacitance dependence of sensor 174 that develop over time. Aspects of drift control are addressed, for example, in PCT Application PCT/IB2013/060038, entitled "Drift compensation for implanted capacitance-based pressure transducer," whose disclosure is incorporated herein by reference.

C-to-F unit 190 converts the capacitance of the pressure sensor (174 or 178) into frequency. Put in another way, unit 190 produces a signal whose frequency is indicative of the capacitance of the pressure sensor (and therefore indicative of the measured ambient pressure). The signal produced by unit 190 is used for modulating a modulation switch 162. Thus, modulation switch 162 is toggled at a frequency that is indicative of the measured ambient pressure. As will be explained further below, switch 162 modulates the load impedance of antenna coil 155. External unit 120 senses the load modulation, measures the modulation frequency and derives the measured pressure therefrom. Typically, switch 162 is normally-closed, so as to allow initial power supply to the implant.

Figure 5:
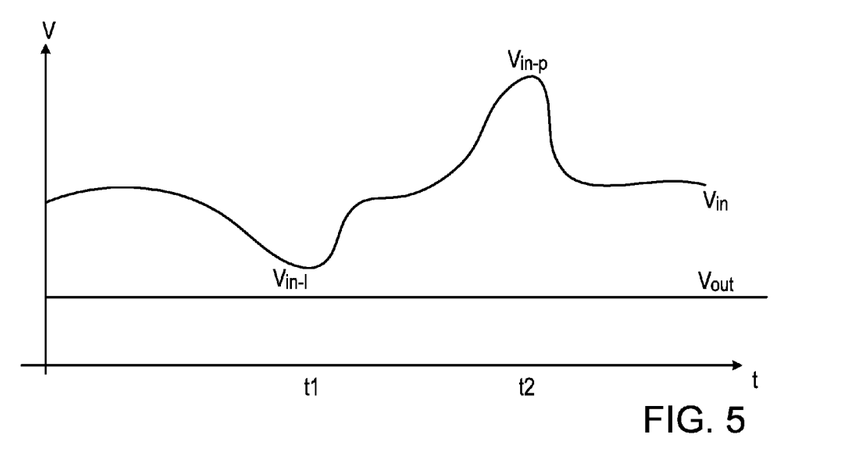
FIG. 5 is a graph showing a process of voltage regulation in a sensory implant, in accordance with an embodiment of the present invention.

FIG. 5 is a graph showing an example of voltage regulation in implant 110, in accordance with an embodiment of the present invention. The top curve (denoted Vin) shows the AC voltage that is induced in coil 155 by the magnetic field generated by external unit 120. As can be seen in the figure, the induced AC voltage oscillates between a minimal voltage denoted Vin-1 (occurring at time tl) and a maximal voltage denoted Vin-p (occurring at time t1). The bottom curve (denoted Vout) shows the rectified and regulated voltage at the output of voltage regulator 166. In one example, Vin oscillates between 2V and 7V, and Vout is somewhat below 2V. Generally, however, any other suitable voltages can be used.

As noted above, in some embodiments implant 110 transmits the measured pressure readings to external unit 120 by modulating the load impedance of antenna coil 155. The load modulation modulates the energy drawn from the magnetic field of external unit 120. The external unit senses the change in energy consumption from the magnetic field, and in this manner demodulates the data transmitted from the implant. Load modulation is performed using modulation switch 162, which is controlled by C-to-F unit 190.

Figure 6:
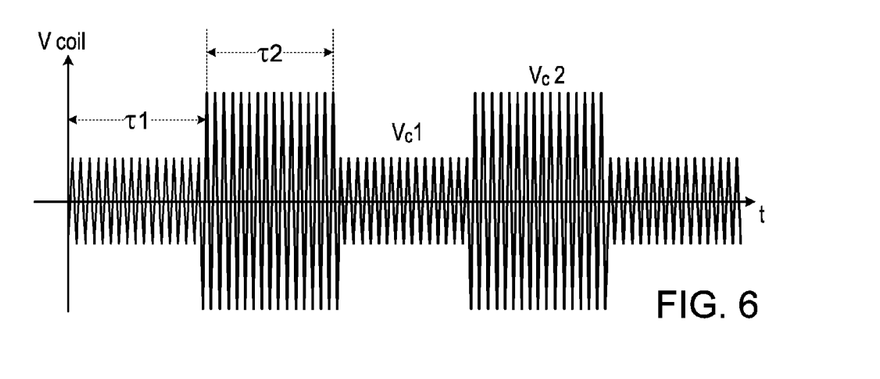
FIG. 6 is a graph showing a voltage in a load-modulated antenna of a sensory implant, in accordance with an embodiment of the present invention.

FIG. 6 is a graph showing the voltage across antenna coil 155 during load modulation, in accordance with an embodiment of the present invention. The high-frequency carrier frequency shown in the figure is the frequency of the AC magnetic field generated by external unit 120. The lower-frequency square-wave envelope is the modulation envelope generated by modulation switch 162. Typically, the modulation frequency is considerably lower than the magnetic-field frequency, e.g., one to three orders of magnitude lower. In one example embodiment, the magnetic-field frequency is approximately 6.78 MHz or 13.56 MHz, and the modulation frequency is approximately 20 Khz (a symbol time of approximately 50 µsec).

Magnetic-field frequencies around 6.78 MHz or 13.56 MHz may be preferred, for example, because they are allocated as Industrial Scientific and Medical (ISM) bands in which relatively high field strength emission is allowed. At the same time, these frequencies are suitable for inductive coupling and suffer little attenuation in body tissue. Alternatively, however, other suitable frequencies can also be chosen.

In the example of FIG. 6, the load modulation alternates between two values, corresponding to voltages denoted Vc1 and Vc2. The lower value (Vc1) is produced by closing modulation switch 162 (thereby drawing more energy from the magnetic field and lowering the voltage induced across antenna coil 155). The higher value (Vc2) is produced by opening modulation switch 162 (thereby drawing less energy from the magnetic field and increasing the voltage induced across antenna coil 155).

In the present example Vc1=3.5V and Vc2=8V. The symbol times of these values are denoted τ1 and τ2. In the present example, τ1=τ2=25 µs, although the symbol times are not necessarily equal. Alternatively, any other suitable values can be used. When using load modulation, the equivalent load impedance of antenna coil 155 (which determines the amount of energy drawn from the magnetic field) depends on various factors, such as the resistance of coil 155 (at the frequency of the AC magnetic field including possible skin effects), the Q-factor of resonant circuit 154 (or of coil 155 alone if capacitor 156 is omitted), and the coupling strength between the antenna of external unit 120 and coil 155.

Among other factors, the reliability of the load-modulation communication technique depends on the modulation depth, i.e., the difference between Vc1 and Vc2. Higher modulation depth makes it easier for the external unit to reliably decode the transmitted data.

Figure 7:
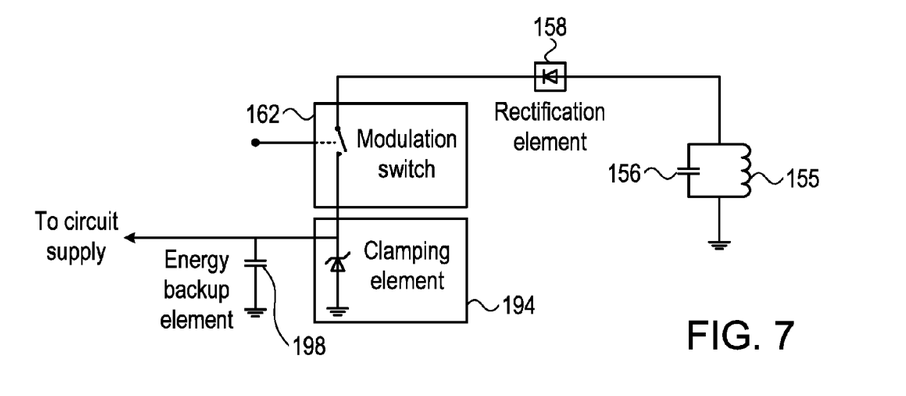
FIG. 7 is a block diagram that schematically illustrates joint load modulation and power supply circuitry in a sensory implant, in accordance with an embodiment of the present invention.

FIG. 7 is a block diagram that schematically illustrates joint load modulation and power supply circuitry in implant 110, in accordance with an embodiment of the present invention. In addition to elements already seen in FIG. 4 above (coil 155, capacitor 156, rectifier 158 and modulation switch 162) this example circuit also comprises a voltage clamping element 194 and an energy backup element (typically capacitor) 198.

Voltage clamping element 194 clamps (e.g., limits) the voltage across its terminals to a predefined maximum value denoted Vclamp. In the present example, element 194 comprises a Zener diode. Various alternatives for implementing the clamping element are given in FIGS. 9A-9C below.

Voltage clamping element 194 serves a dual function in implant 110. The first function is to increase the modulation depth of the load modulation. The second function is to regulate the induced voltage that is subsequently used for powering the implant circuitry.

Consider the function of increasing the modulation depth. In the present example, clamping element 194 and modulation switch 162 are connected in series with one another, and both components are connected across antenna coil 155. When modulation switch 162 is closed, element 194 clamps the voltage induced across antenna coil 155 and presents very low impedance to the antenna coil. When modulation switch 162 is open, very high impedance is presented to the antenna coil. This large difference in load impedance maximizes the modulation depth (e.g., the difference between Vc1 and Vc2 in FIG. 6 above.

At the same time, clamping element 194 helps in regulating the supply voltage drawn from the induced magnetic field, in conjunction with capacitor 198. When modulation switch 162 is closed, element 194 clamps the voltage supply voltage to Vclamp, and capacitor 198 is charged using this voltage. When modulation switch 162 is open, the implant circuitry draws power from capacitor 198. The combination of clamping element 194 and capacitor 198 ensures that the resulting supply voltage is stable, notwithstanding the large changes in the induced AC voltage due to the load modulation.

Figure 8:
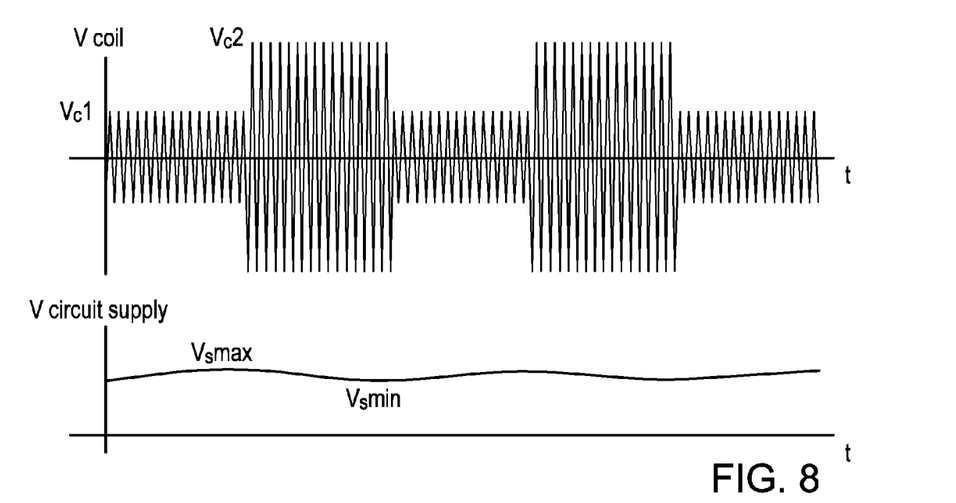
FIG. 8 is a graph showing voltages in a sensory implant that uses joint load modulation and power supply, in accordance with an embodiment of the present invention.

FIG. 8 is a graph that demonstrates this effect, in accordance with an embodiment of the present invention. The top curve shows the voltage induced across antenna coil 155 during load modulation. The bottom curve shows the supply voltage, following clamping and regulation by clamping element 194 and capacitor 198. As can be seen in the figure, the supply voltage is relatively stable (varies between Vsmin and Vsmax, which in the present example differ by only 100 mV). In an alternative embodiment, the circuit may comprise an additional voltage regulator for further stabilizing the supply voltage.

Figure 9A:
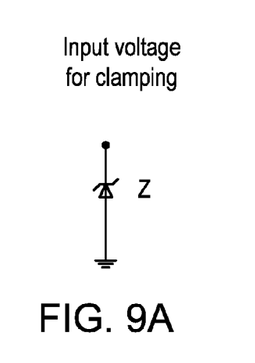
FIGS. 9A-9C are circuit diagrams showing voltage clamping elements, in accordance with embodiments of the present invention.
Figure 9B:
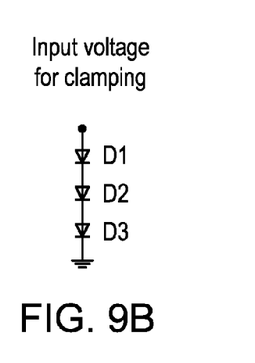
Figure 9C:
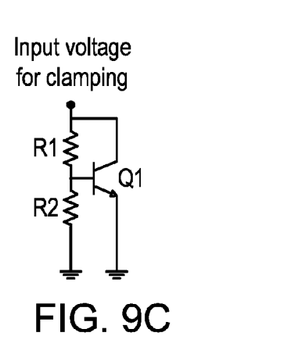

FIGS. 9A-9C are circuit diagrams showing example voltage clamping elements, in accordance with embodiments of the present invention. All these configurations can be used for implementing voltage clamping element 194. The configurations of FIGS. 9A-9C are depicted purely by way of example. In alternative embodiments, any other suitable implementation can be used.

In FIG. 9A, the voltage clamping element comprises a single Zener diode denoted Z, which is connected for backward conduction relative to the supply voltage. In an example embodiment, the clamping voltage Vclamp of the diode is 1.8V. In FIG. 9B, the voltage clamping element comprises one or more diodes, e.g., three diodes D1 . . . D3, connected in series in forward conduction relative to the supply voltage.

In the example of FIG. 9B, diodes D1 . . . D3 comprise silicon diodes, the forward voltage of each diode is thus ~0.6V, and therefore the cascade of three diodes performs clamping at ~1.8V. In alternative embodiments, the desired clamping voltage can be set using a suitable combination of one or more silicon diodes (having a forward voltage of ~0.6V) and one or more Schottky diodes (having a forward voltage of ~0.2V). A combination of one or more forward-conducting diodes (e.g., silicon or Schottky) and one or more backward-conducting Zener diodes is also possible.

In FIG. 9C, the voltage clamping element is implemented using a semiconductor element circuit having the desired fixed forward voltage. In the present example, the circuit comprises a transistor denoted Q1 and two resistors denoted R1 and R2. In an example implementation, R1=68 KΩ, R2=22 KΩ, and Q1 has a base-emitter voltage Be=0.5V, resulting in a clamping voltages of approximately 1.82V. In alternative embodiments, any other suitable clamping circuit, e.g., formed from discrete components, can be used.

Figure 10:
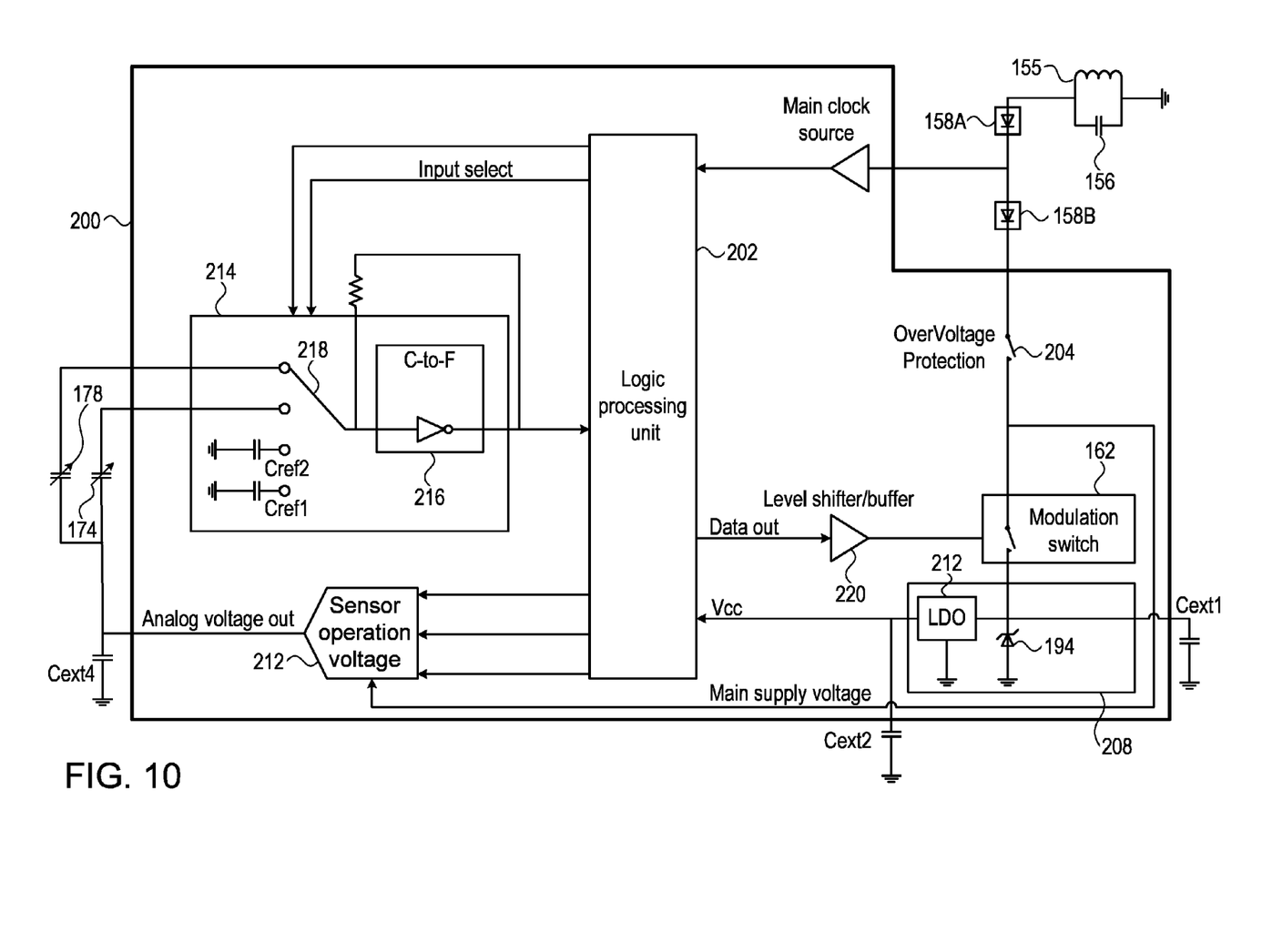
FIG. 10 is a block diagram that schematically illustrates control circuitry of a sensory implant, in accordance with an embodiment of the present invention.

FIG. 10 is a block diagram that schematically illustrates control circuitry of implant 110, in accordance with an embodiment of the present invention. In some embodiments, most or all of the control circuitry is implemented in a mixed-signal Application-Specific Integrated Circuit (ASIC) 200. Some elements, e.g., pressure sensor 174, reference sensor 178, antenna coil 155 and capacitor 156, rectifiers 158A and 158B, and several capacitors, are typically external to the ASIC.

In the present example, ASIC 200 comprises a logic processing unit 202 that controls the ASIC operation. A modulator 214 comprises a C-to-F converter 216, which produces a square wave whose frequency depends on the input capacitance. An input selection switch 218 selects among several capacitances that can be provided as input to the C-to-F converter.

In the present example, switch 218 selects among real MEMS pressure sensor 174 (which measures the ambient blood pressure), reference MEMS pressure sensor 178, and two fixed reference capacitors denoted Cref1 and Cref2. Switch 218 is controlled by unit 202 using "INPUT SELECT" lines.

A sensor operation voltage module 212, typically comprising a digital-to-analog converter, provides a suitable analog operation voltage for the MEMS pressure sensors. The analog voltage is adjusted by unit 202, for example using discrete control lines to module 212. One reason for adjusting this voltage is as part of a drift compensation process, as described in PCT Application PCT/IB2013/060038, cited above.

For data transmission from the implant, logic processing unit 202 produces a digital signal denoted "data out," whose frequency follows the output of C-to-F converter 216. In other words, the binary code of the "data out" signal depends on the capacitance of the MEMS pressure sensor (or other capacitance selected by switch 218). A level shifter/buffer 220 buffers the signal and drives modulation switch 162. The variable-frequency signal thus modulates the load impedance of antenna coil 155, as explained above.

For providing electrical power to ASIC 200, rectifiers 158A and 158B rectify the AC voltage induced in antenna coil 155. An over-voltage protection switch protects the ASIC from high-voltage surges. The rectified voltage is regulated by a regulation unit 208. In unit 208, the voltage is clamped by clamping element 194, as explained above. An external capacitor denoted Cextl serves as energy backup element (similar to element 198 of FIG. 7). A low Drop-Off (LDO) regulator 212 further regulates the supply voltage. The output of LDO regulator 212 is provided as the supply voltage (Vcc) of ASIC 200.

As explained above, voltage clamping element 194 in unit 208 plays a dual role—

Maximizes the modulation depth of the load modulation scheme, and regulates the supply voltage for ASIC 200. A "main clock source" module derives a clock signal for the ASIC from the induced AC voltage, similarly to clock extraction module 170 of FIG. 7. In an alternative embodiment, the main clock source may be generated by the ASIC.

Data Balancing for Ensuring Sufficient Power Supply

As can be seen in the examples of FIGS. 6 and 8 above, the average voltage (and thus the average power) induced in antenna coil 155 fluctuates considerably as a result of load modulation. Since the induced voltage depends on the modulated bit values, certain bit patterns may translate into long periods of low voltage. In such an event, there is a risk that the power supplied to implant 110 will not be sufficient. There is also a risk that the binary bits content will affect the regulated voltage level, and as a result will shift the result of the C-to-F unit, since the C-to-F unit may be sensitive to the voltage supply level.

In some embodiments, ASIC 200 uses a load modulation scheme that prevents the problematic scenario described above. Typically, logic processing unit 202 balances the data to be load-modulated, such that the electrical energy received from the induced magnetic field meets the power requirements of the circuitry regardless of the actual data values.

Unit 202 may balance the data in various ways. In an example embodiment, unit 202 uses a balanced modulation scheme that represents each bit value with a respective symbol having a positive-voltage part and a negative-voltage part. For example, unit 202 may represent each "0" bit value with a symbol equal to +V during the first half of the symbol and to −V during the second half of the symbol, and each "1" bit value with a symbol equal to −V during the first half of the symbol and to +V during the second half of the symbol.

Put in another way, unit 202 may modulate each data value twice, with opposite polarities. When performing load modulation using such schemes, the average power of the induced voltage remains substantially constant regardless of the data values. Alternatively, any other suitable balancing scheme can be used.

Noise Cancellation

ASIC 200 and implant 110 in general often operate in the presence of strong interference. One source of interference is Radio Frequency (RF) interference at the frequency of the AC magnetic field of the external unit (6.78 MHz in the examples described herein). Other sources of interference may also exist.

Some parts of the implant circuitry, for example C-to-F converter 216, operate on weak signals with high accuracy and are therefore sensitive to interference. Unless accounted for, this interference may cause considerable degradation in the overall measurement accuracy and reliability of implant 110. In some embodiments, implant 110 comprises mechanisms for interference mitigation.

Figure 11:
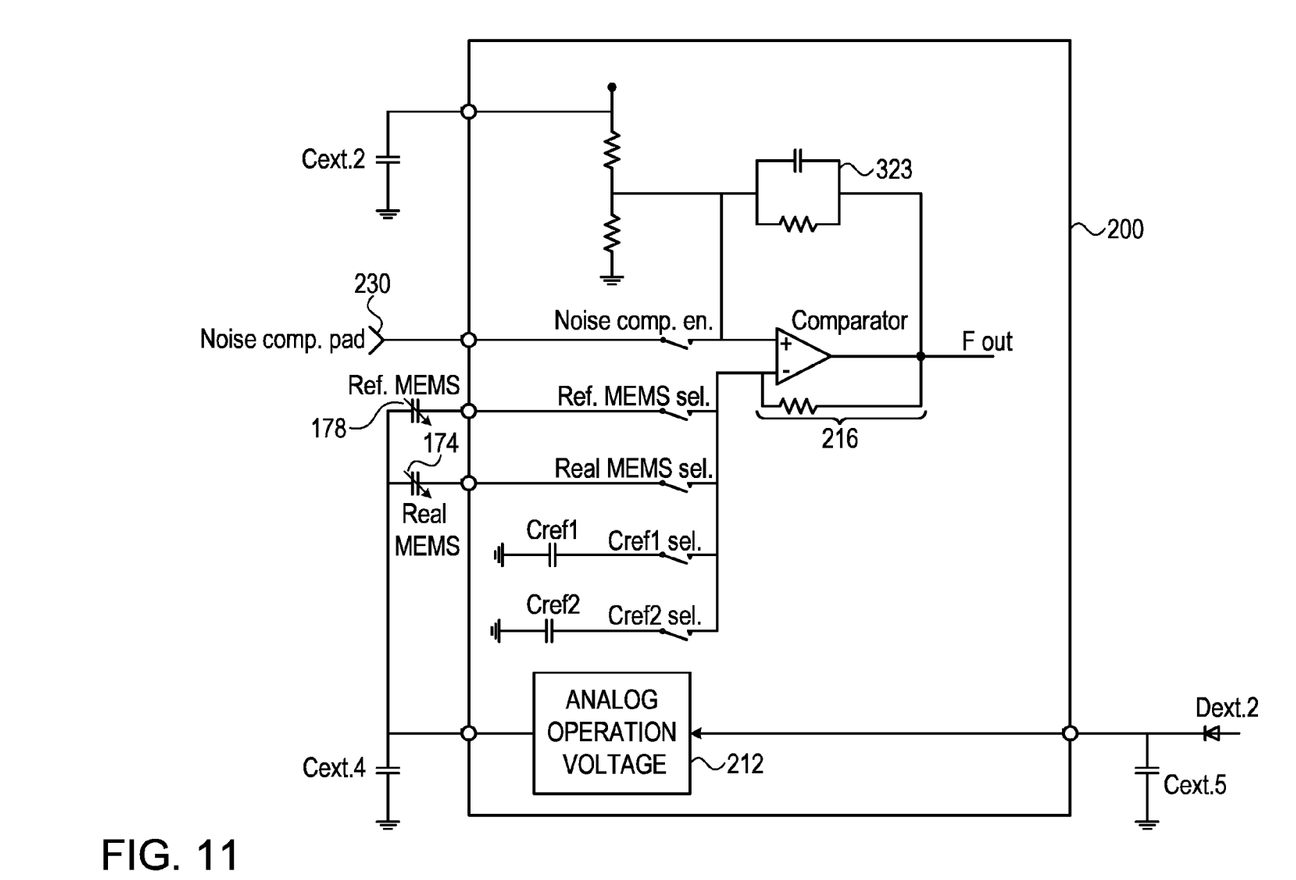
FIG. 11 is a block diagram that schematically illustrates elements of control circuitry of a sensory implant, in accordance with an embodiment of the present invention.

FIG. 11 is a block diagram that schematically illustrates elements of control circuitry of implant 110, in accordance with an embodiment of the present invention. In this example, C-to-F converter 216 comprises an oscillator circuit built around a comparator. Pressure sensor 174 (or other capacitance selected for calibration purposes using a respective switch) is connected to one of its inputs. A feedback path from the comparator output to the comparator input comprises a resistor-capacitor pair 232. The oscillation frequency of the oscillator (denoted Fout) is determined by the capacitance of pressure sensor 174, and by the resistance and capacitance of resistor-capacitor pair 232.

In the embodiment of FIG. 11, implant 110 further comprises a noise compensation antenna, in the present example a noise compensation pad 230. Pad 230 is designed and fabricated so as to receive a similar level of RF interference as pressure sensor 174. In an example implementation, pad 230 may comprises a metallic patch that is printed on an internal Printed Circuit Board (PCB) of implant 110 and connected to an input pin of ASIC 200. The ASIC comprises a "noise compensation enable" switch, which is controlled by unit 202 so as to connect or disconnect pad 230 as needed. Alternatively, any other suitable type of interference compensation antenna can be used.

When compensation is enabled, pressure sensor 174 is connected to one input of the comparator and pad 230 is connected to the other input. Pad 230 is typically designed such that the impedances at the two comparator inputs are substantially the same. As a result, the RF interference levels applied to the two comparator inputs are also substantially the same, and interference cancellation at the comparator output is optimal.

In some embodiments, the noise cancellation accuracy can also be controlled by adjusting the resistance and/or capacitance of resistor-capacitor pair 232. In one embodiment, the resistance and/or capacitance of resistor-capacitor pair are programmable remotely by external unit 120. In this embodiment, external unit 120 calibrates the resistance and/or capacitance of resistor-capacitor pair 232 so as to minimize the interference level. This calibration can be performed, for example, at the beginning of each pressure measurement session, upon detecting that interference is high, or at any other suitable time.

Although the embodiments described herein mainly address wireless implantable hemodynamic measurements, the implantable devices and associated methods described herein can also be used in other applications, such as in intraocular pressure (IOP) monitoring for better treatment of glaucoma, in bladder pressure monitoring, e.g., as a diagnostic tool for urology, or in measuring blood pressure in the aorta, renal artery, femoral artery or radial artery, e.g., for better management of hypertension patients. As another example, the disclosed techniques can be used for measuring pulmonary artery pressure for better management of heart failure patients. As yet another example, the disclosed techniques can be used for intracranial pressure (ICP) monitoring, which can aid in the management of neurological disorders such as hydrocephalus, head trauma, tumors, colloid cysts and cerebral hematomas. As can be appreciated, the disclosed techniques are in no way limited to pressure measurements and can be used for wireless in-body sensing of any suitable parameter.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An implant, comprising:
   an antenna, which is configured to communicate with an external unit using inductive coupling of a magnetic field;
   circuitry, which is configured to produce data for transmission to the external unit, and to receive electrical power from the magnetic field via the antenna for powering the circuitry;
   a voltage clamping element, which is coupled to clamp a voltage induced by the magnetic field across the antenna; and
   a modulation switch, configured to modulate a load impedance applied to the antenna as a function of the data, so as to transmit the data,
   wherein the electrical power that powers the circuitry is provided to the circuitry from a connection point between the modulation switch and the voltage clamping element, such that the circuitry is disconnected from the antenna while the modulation switch is open.

2. The implant according to claim 1, wherein the voltage clamping element applies a low load impedance across the antenna only when the modulation switch is closed.

3. The implant according to claim 1, wherein the voltage clamping element comprises at least one Zener diode.

4. The implant according to claim 1, wherein the voltage clamping element comprises one or more diodes connected in forward conduction relative to the voltage.

5. The implant according to claim 1, wherein the voltage clamping element comprises a transistor circuit.

6. The implant according to claim 1, wherein the modulation switch and the voltage clamping element are connected in series to one another at the connection point, and wherein the serially-connected modulation switch and voltage clamping element are connected across the antenna.

7. The implant according to claim 1, further comprising an energy backup element, wherein: while the modulation switch is closed, the electrical power is provided to the circuitry from the antenna and also charges the energy backup element; and while the modulation switch is open and the circuitry is disconnected from the antenna, the electrical power is provided to the circuitry from the energy backup element.

8. A method for operating an implant, the method comprising:
   producing, using circuitry in the implant, data for transmission to an external unit, and modulating a load impedance applied to an antenna using a modulation switch as a function of the data so as to transmit the data to the external unit using inductive coupling of a magnetic field;
   receiving via the antenna electrical power from the magnetic field for powering the circuitry; and
   using a voltage clamping element, clamping a voltage induced by the magnetic field across the antenna,
   wherein the electrical power that powers the circuitry is provided to the circuitry from a connection point between the modulation switch and the voltage clamping element, such that the circuitry is disconnected from the antenna while the modulation switch is open.

9. The method according to claim 8, wherein the voltage clamping element comprises at least one Zener diode.

10. The method according to claim 8, wherein the voltage clamping element comprises one or more diodes connected in forward conduction relative to the voltage.

11. The method according to claim 8, wherein the voltage clamping element comprises a transistor circuit.

12. The method according to claim 8, wherein the modulation switch and the voltage clamping element are connected in series to one another at the connection point, and wherein the serially-connected modulation switch and voltage clamping element are connected across the antenna.

13. The method according to claim 8, further comprising:
    while the modulation switch is closed, providing the electrical power to the circuitry from the antenna and also charging an energy backup element; and
    while the modulation switch is open and the circuitry is disconnected from the antenna, providing the electrical power to the circuitry from the energy backup element.

* * * * *